(12) United States Patent
Krastins

(10) Patent No.: US 12,295,641 B2
(45) Date of Patent: May 13, 2025

(54) ELECTROSURGICAL FORCEPS WITH SWIVEL ACTION NERVE PROBE

(71) Applicant: Covidien LP, Mansfield, MA (US)

(72) Inventor: Craig V. Krastins, Arvada, CO (US)

(73) Assignee: Covidien LP, Mansfield, MA (US)

( * ) Notice: Subject to any disclaimer, the term of this patent is extended or adjusted under 35 U.S.C. 154(b) by 903 days.

(21) Appl. No.: 17/360,281

(22) Filed: Jun. 28, 2021

(65) Prior Publication Data

US 2022/0000541 A1 Jan. 6, 2022

Related U.S. Application Data

(60) Provisional application No. 63/046,861, filed on Jul. 1, 2020.

(51) Int. Cl.
*A61B 18/00* (2006.01)
*A61B 18/12* (2006.01)
*A61B 18/14* (2006.01)

(52) U.S. Cl.
CPC ...... *A61B 18/1445* (2013.01); *A61B 18/1206* (2013.01); *A61B 2018/00184* (2013.01); *A61B 2018/00434* (2013.01); *A61B 2018/00601* (2013.01); *A61B 2018/1475* (2013.01)

(58) Field of Classification Search
None
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| 4,543,959 A | 10/1985 | Sepponen |
| D295,893 S | 5/1988 | Sharkany et al. |
| D295,894 S | 5/1988 | Sharkany et al. |
| 4,763,669 A | 8/1988 | Jaeger |
| D298,353 S | 11/1988 | Manno |
| D299,413 S | 1/1989 | DeCarolis |
| 5,100,420 A | 3/1992 | Green et al. |
| 5,258,001 A | 11/1993 | Corman |
| D343,453 S | 1/1994 | Noda |
| 5,304,203 A | 4/1994 | El-Mallawany et al. |
| D348,930 S | 7/1994 | Olson |
| D349,341 S | 8/1994 | Lichtman et al. |
| 5,344,424 A | 9/1994 | Roberts et al. |
| D354,564 S | 1/1995 | Medema |
| D358,887 S | 5/1995 | Feinberg |

(Continued)

FOREIGN PATENT DOCUMENTS

WO    2006042117 A2    4/2006

*Primary Examiner* — Linda C Dvorak
*Assistant Examiner* — Nicholas S Borsch

(57) ABSTRACT

An electrosurgical forceps includes first and second shaft members each having a jaw member disposed at a distal end thereof and configured to rotate about a pivot to move the jaw members between an open position and a closed position, the first and second shaft members defining a longitudinal axis therebetween. A nerve monitoring probe is operably associated with one of the shaft members and is selectively movable relative to the longitudinal axis between a first, at rest position wherein the nerve monitoring probe is aligned with the longitudinal axis and a second, deployed position wherein the nerve monitoring probe is positioned at an angle relative to the longitudinal axis for nerve monitoring.

13 Claims, 2 Drawing Sheets

(56) References Cited

U.S. PATENT DOCUMENTS

| | | |
|---|---|---|
| 5,540,685 A | 7/1996 | Parins et al. |
| 5,578,052 A | 11/1996 | Koros et al. |
| 5,611,808 A | 3/1997 | Hossain et al. |
| 5,618,294 A | 4/1997 | Aust et al. |
| D384,413 S | 9/1997 | Zlock et al. |
| 5,665,100 A | 9/1997 | Yoon |
| 5,752,644 A | 5/1998 | Bolanos et al. |
| H1745 H | 8/1998 | Paraschac |
| 5,800,350 A | 9/1998 | Coppleson et al. |
| 5,814,043 A | 9/1998 | Shapeton |
| D402,028 S | 12/1998 | Grimm et al. |
| D408,018 S | 4/1999 | McNaughton |
| 5,913,874 A | 6/1999 | Berns et al. |
| 5,960,544 A | 10/1999 | Beyers |
| D416,089 S | 11/1999 | Barton et al. |
| 6,050,996 A | 4/2000 | Schmaltz et al. |
| D424,694 S | 5/2000 | Tetzlaff et al. |
| D425,201 S | 5/2000 | Tetzlaff et al. |
| 6,109,268 A | 8/2000 | Thapliyal et al. |
| H1904 H | 10/2000 | Yates et al. |
| 6,241,725 B1 | 6/2001 | Cosman |
| 6,293,954 B1 | 9/2001 | Fogarty et al. |
| D449,886 S | 10/2001 | Tetzlaff et al. |
| 6,329,778 B1 | 12/2001 | Culp et al. |
| 6,334,861 B1 | 1/2002 | Chandler et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| 6,406,485 B1 | 6/2002 | Hossain et al. |
| H2037 H | 7/2002 | Yates et al. |
| 6,428,537 B1 | 8/2002 | Swanson et al. |
| 6,464,704 B2 | 10/2002 | Schmaltz et al. |
| D465,281 S | 11/2002 | Lang |
| D466,209 S | 11/2002 | Bon |
| 6,511,480 B1 | 1/2003 | Tetzlaff et al. |
| 6,546,270 B1 | 4/2003 | Goldin et al. |
| 6,564,078 B1 * | 5/2003 | Marino ............... A61N 1/0551 607/116 |
| 6,569,160 B1 | 5/2003 | Goldin et al. |
| 6,673,092 B1 | 1/2004 | Bacher |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,089,045 B2 | 8/2006 | Fuimaono et al. |
| 7,099,712 B2 | 8/2006 | Fuimaono et al. |
| D531,311 S | 10/2006 | Guerra et al. |
| 7,118,570 B2 | 10/2006 | Tetzlaff et al. |
| D533,274 S | 12/2006 | Visconti et al. |
| D533,942 S | 12/2006 | Kerr et al. |
| 7,155,270 B2 | 12/2006 | Solis et al. |
| D535,027 S | 1/2007 | James et al. |
| D538,932 S | 3/2007 | Malik |
| D541,418 S | 4/2007 | Schechter et al. |
| 7,207,989 B2 | 4/2007 | Pike, Jr. et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| 7,257,434 B2 | 8/2007 | Fuimaono et al. |
| 7,257,435 B2 | 8/2007 | Plaza |
| 7,329,257 B2 | 2/2008 | Kanehira et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,431,730 B2 | 10/2008 | Viola |
| D582,038 S | 12/2008 | Swoyer et al. |
| 7,641,653 B2 | 1/2010 | Dalla Betta et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| 7,819,860 B2 | 10/2010 | Wittenberger et al. |
| D627,462 S | 11/2010 | Kingsley |
| D628,289 S | 11/2010 | Romero |
| D628,290 S | 11/2010 | Romero |
| 7,854,185 B2 | 12/2010 | Zhang et al. |
| D630,324 S | 1/2011 | Reschke |
| 7,896,878 B2 | 3/2011 | Johnson et al. |
| D649,249 S | 11/2011 | Guerra |
| D649,643 S | 11/2011 | Allen, IV et al. |
| 8,147,489 B2 | 4/2012 | Moses et al. |
| D661,394 S | 6/2012 | Romero et al. |
| 8,298,233 B2 | 10/2012 | Mueller |
| D670,808 S | 11/2012 | Moua et al. |
| 8,366,709 B2 | 2/2013 | Schechter et al. |
| 8,394,096 B2 | 3/2013 | Moses et al. |
| D680,220 S | 4/2013 | Rachlin |
| 8,409,246 B2 | 4/2013 | Kerr et al. |
| 8,409,247 B2 | 4/2013 | Garrison et al. |
| 8,425,504 B2 | 4/2013 | Orton et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,591,510 B2 | 11/2013 | Allen, IV et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,858,553 B2 | 10/2014 | Chojin |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,888,775 B2 | 11/2014 | Nau, Jr. et al. |
| 8,898,888 B2 | 12/2014 | Brandt et al. |
| 8,900,232 B2 | 12/2014 | Ourada |
| 8,906,018 B2 | 12/2014 | Rooks et al. |
| 8,920,421 B2 | 12/2014 | Rupp |
| 8,932,293 B2 | 1/2015 | Chernov et al. |
| 8,936,614 B2 | 1/2015 | Allen, IV |

(56) References Cited

U.S. PATENT DOCUMENTS

| | | |
|---|---|---|
| 8,939,972 B2 | 1/2015 | Twomey |
| 8,945,175 B2 | 2/2015 | Twomey |
| 8,961,504 B2 | 2/2015 | Hoarau et al. |
| 8,968,283 B2 | 3/2015 | Kharin |
| 8,968,305 B2 | 3/2015 | Dumbauld et al. |
| 8,968,316 B2 | 3/2015 | Roy et al. |
| 8,968,357 B2 | 3/2015 | Mueller |
| 8,968,359 B2 | 3/2015 | Kerr et al. |
| 9,005,200 B2 | 4/2015 | Roy et al. |
| 9,017,372 B2 | 4/2015 | Artale et al. |
| 9,028,484 B2 | 5/2015 | Craig |
| 9,028,492 B2 | 5/2015 | Kerr et al. |
| 9,028,495 B2 | 5/2015 | Mueller et al. |
| 9,039,704 B2 | 5/2015 | Joseph |
| 9,039,732 B2 | 5/2015 | Sims et al. |
| 9,084,608 B2 | 7/2015 | Larson et al. |
| 9,113,933 B2 | 8/2015 | Chernova et al. |
| 9,113,934 B2 | 8/2015 | Chernov et al. |
| 9,161,807 B2 | 10/2015 | Garrison |
| 9,211,657 B2 | 12/2015 | Ackley et al. |
| 9,265,568 B2 | 2/2016 | Chernov et al. |
| 9,333,002 B2 | 5/2016 | Garrison |
| 9,381,059 B2 | 7/2016 | Garrison |
| 9,456,870 B2 | 10/2016 | Chernov et al. |
| 9,498,278 B2 | 11/2016 | Couture et al. |
| 9,498,279 B2 | 11/2016 | Artale et al. |
| 9,504,519 B2 | 11/2016 | Kerr et al. |
| 9,585,709 B2 | 3/2017 | Krapohl |
| 9,615,877 B2 | 4/2017 | Tyrrell et al. |
| 9,655,672 B2 | 5/2017 | Artale et al. |
| 10,973,567 B2 | 4/2021 | Sims et al. |
| 2002/0099372 A1* | 7/2002 | Schulze .............. A61B 18/1445 606/171 |
| 2003/0018332 A1 | 1/2003 | Schmaltz et al. |
| 2003/0045798 A1 | 3/2003 | Hular et al. |
| 2003/0109875 A1 | 6/2003 | Tetzlaff et al. |
| 2003/0120306 A1 | 6/2003 | Burbank et al. |
| 2003/0199869 A1 | 10/2003 | Johnson et al. |
| 2003/0220637 A1 | 11/2003 | Truckai et al. |
| 2003/0229344 A1 | 12/2003 | Dycus et al. |
| 2004/0092927 A1 | 5/2004 | Podhajsky et al. |
| 2004/0193153 A1 | 9/2004 | Sartor et al. |
| 2005/0027199 A1 | 2/2005 | Clarke |
| 2005/0070889 A1 | 3/2005 | Nobis et al. |
| 2005/0107784 A1 | 5/2005 | Moses et al. |
| 2005/0113826 A1 | 5/2005 | Johnson et al. |
| 2005/0113828 A1 | 5/2005 | Shields et al. |
| 2005/0159745 A1 | 7/2005 | Truckai et al. |
| 2006/0106375 A1 | 5/2006 | Werneth et al. |
| 2006/0253126 A1 | 11/2006 | Bjerken et al. |
| 2007/0062017 A1 | 3/2007 | Dycus et al. |
| 2007/0088356 A1 | 4/2007 | Moses et al. |
| 2007/0106289 A1 | 5/2007 | O'Sullivan |
| 2007/0156128 A1 | 7/2007 | Jimenez |
| 2007/0167943 A1 | 7/2007 | Janssen et al. |
| 2007/0179499 A1 | 8/2007 | Garrison |
| 2007/0248254 A1 | 10/2007 | Mysore Siddu et al. |
| 2007/0260241 A1 | 11/2007 | Dalla Betta et al. |
| 2008/0065178 A1 | 3/2008 | Kelleher et al. |
| 2008/0215048 A1 | 9/2008 | Hafner et al. |
| 2009/0131934 A1 | 5/2009 | Odom et al. |
| 2009/0163904 A1 | 6/2009 | Miller et al. |
| 2009/0171353 A1 | 7/2009 | Johnson et al. |
| 2009/0182327 A1 | 7/2009 | Unger |
| 2009/0240246 A1 | 9/2009 | Deville et al. |
| 2009/0267773 A1 | 10/2009 | Markowitz et al. |
| 2009/0302090 A1 | 12/2009 | Shah |
| 2009/0308909 A1 | 12/2009 | Nalagatla et al. |
| 2010/0016857 A1 | 1/2010 | McKenna et al. |
| 2010/0130977 A1 | 5/2010 | Garrison et al. |
| 2010/0179545 A1 | 7/2010 | Twomey et al. |
| 2010/0179547 A1 | 7/2010 | Cunningham et al. |
| 2010/0228250 A1 | 9/2010 | Brogna |
| 2010/0274244 A1 | 10/2010 | Heard |
| 2010/0292691 A1 | 11/2010 | Brogna |
| 2010/0305567 A1 | 12/2010 | Swanson |
| 2011/0054469 A1 | 3/2011 | Kappus et al. |
| 2011/0060314 A1 | 3/2011 | Wallace et al. |
| 2011/0060356 A1 | 3/2011 | Reschke et al. |
| 2011/0072638 A1 | 3/2011 | Brandt et al. |
| 2011/0087218 A1 | 4/2011 | Boudreaux et al. |
| 2011/0218530 A1 | 9/2011 | Reschke |
| 2011/0238065 A1 | 9/2011 | Hunt et al. |
| 2011/0238067 A1 | 9/2011 | Moses et al. |
| 2011/0257680 A1 | 10/2011 | Reschke et al. |
| 2011/0270121 A1* | 11/2011 | Johnson .............. A61B 17/29 606/51 |
| 2011/0270245 A1 | 11/2011 | Horner et al. |
| 2011/0270251 A1 | 11/2011 | Horner et al. |
| 2011/0276049 A1 | 11/2011 | Gerhardt |
| 2011/0295313 A1 | 12/2011 | Kerr |
| 2012/0059372 A1 | 3/2012 | Johnson |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172873 A1 | 7/2012 | Artale et al. |
| 2012/0172924 A1 | 7/2012 | Allen, IV |
| 2012/0184988 A1 | 7/2012 | Twomey et al. |
| 2012/0184989 A1 | 7/2012 | Twomey |
| 2012/0184990 A1 | 7/2012 | Twomey |
| 2012/0209263 A1 | 8/2012 | Sharp et al. |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0000463 A1 | 1/2013 | Evans et al. |
| 2013/0018364 A1 | 1/2013 | Chernov et al. |
| 2013/0018372 A1 | 1/2013 | Sims et al. |
| 2013/0018411 A1 | 1/2013 | Collings et al. |
| 2013/0022495 A1 | 1/2013 | Allen, IV et al. |
| 2013/0030432 A1 | 1/2013 | Garrison et al. |
| 2013/0041370 A1 | 2/2013 | Unger |
| 2013/0046295 A1 | 2/2013 | Kerr et al. |
| 2013/0046306 A1 | 2/2013 | Evans et al. |
| 2013/0046337 A1 | 2/2013 | Evans et al. |
| 2013/0060250 A1 | 3/2013 | Twomey et al. |
| 2013/0066318 A1 | 3/2013 | Kerr |
| 2013/0071282 A1 | 3/2013 | Fry |
| 2013/0072927 A1 | 3/2013 | Allen, IV et al. |
| 2013/0079760 A1 | 3/2013 | Twomey et al. |
| 2013/0079762 A1 | 3/2013 | Twomey et al. |
| 2013/0079774 A1 | 3/2013 | Whitney et al. |
| 2013/0085491 A1 | 4/2013 | Twomey et al. |
| 2013/0085496 A1 | 4/2013 | Unger et al. |
| 2013/0103030 A1* | 4/2013 | Garrison .............. A61B 18/1442 606/45 |
| 2013/0103031 A1 | 4/2013 | Garrison |
| 2013/0103035 A1 | 4/2013 | Horner et al. |
| 2013/0123837 A1 | 5/2013 | Roy et al. |
| 2013/0138101 A1 | 5/2013 | Kerr |
| 2013/0138102 A1 | 5/2013 | Twomey et al. |
| 2013/0138129 A1 | 5/2013 | Garrison et al. |
| 2013/0144284 A1 | 6/2013 | Behnke, II et al. |
| 2013/0178852 A1 | 7/2013 | Allen, IV et al. |

(56) References Cited

U.S. PATENT DOCUMENTS

| | | |
|---|---|---|
| 2013/0185922 A1 | 7/2013 | Twomey et al. |
| 2013/0190753 A1 | 7/2013 | Garrison |
| 2013/0190760 A1 | 7/2013 | Allen, IV |
| 2013/0197503 A1 | 8/2013 | Orszulak |
| 2013/0226177 A1 | 8/2013 | Brandt |
| 2013/0267874 A1* | 10/2013 | Marcotte ............ A61B 5/4893 606/41 |
| 2013/0310823 A1* | 11/2013 | Gelfand ............ A61M 25/0082 606/41 |
| 2014/0221994 A1 | 8/2014 | Reschke |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 | 11/2014 | Hart et al. |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0066076 A1 | 3/2015 | Kerr et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |
| 2016/0157922 A1 | 6/2016 | Lee et al. |
| 2016/0157925 A1 | 6/2016 | Artale et al. |
| 2016/0175031 A1 | 6/2016 | Boudreaux |
| 2017/0020601 A1 | 1/2017 | Thomson et al. |
| 2017/0128120 A1 | 5/2017 | Cho et al. |

\* cited by examiner

ELECTROSURGICAL FORCEPS WITH SWIVEL ACTION NERVE PROBE

CROSS REFERENCE TO RELATED APPLICATIONS

This application claims the benefit of U.S. Provisional Application Ser. No. 63/046,861, filed Jul. 1, 2020, the entire contents of which are incorporated by reference herein.

BACKGROUND

Technical Field

The present disclosure relates to electrosurgical instruments and, more particularly, to electrosurgical forceps for grasping, treating, and/or dividing tissue. Background of Related Art A surgical forceps or hemostat is a plier-like instrument which relies on mechanical action between its jaws to grasp tissue. Electrosurgical forceps utilize both mechanical clamping action and electrical energy to treat tissue, e.g., coagulate, cauterize, and/or seal tissue.

Typically, once tissue is treated, the surgeon has to accurately sever the treated tissue. Accordingly, many electrosurgical hemostats have been designed which incorporate a knife configured to effectively sever tissue after treating the tissue.

During a given surgical procedure, it may be advantageous to utilize a probe to monitor nerves that may be encountered in order to ensure functionality post surgery. For example, typical ear, nose and throat (ENT) surgical procedures (e.g., Thyroidectomy, Parathyroidectomy, Parotidectomy, Neck Dissections, etc.) have critical nerves that cannot be damaged during surgery. During these procedures, a nerve monitoring system is utilized to monitor nerves to ensure functionality.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

An electrosurgical forceps provided in accordance with aspects of the present disclosure includes first and second shaft members each having a jaw member disposed at a distal end thereof and configured to rotate about a pivot to move the jaw members between an open position and a closed position, the first and second shaft members defining a longitudinal axis therebetween. A nerve monitoring probe is operably associated with one or more of the shaft members and is selectively movable relative to the longitudinal axis between a first, at rest position wherein the nerve monitoring probe is aligned with the longitudinal axis and a second, deployed position wherein the nerve monitoring probe is positioned at an angle relative to the longitudinal axis for nerve monitoring.

In aspects according to the present disclosure, the nerve monitoring probe is automatically activated when disposed in the deployed position. In other aspects according to the present disclosure, the nerve monitoring probe is operably coupled to at least one shaft member by a pivot.

In aspects according to the present disclosure, the nerve monitoring probe is adapted to connect to an electrosurgical generator including a nerve monitoring system. In other aspects according to the present disclosure, the nerve monitoring probe is adapted to connect to a nerve monitoring system.

In aspects according to the present disclosure, the nerve monitoring probe is only activatable when the jaw members are disposed in an approximated position. In other aspects according to the present disclosure, the nerve monitoring probe is only activatable when the jaw members are disposed in an open position. In yet other aspects according to the present disclosure, the nerve monitoring probe is only activatable when the activation button is inactive.

In aspects according to the present disclosure, the nerve monitoring probe is housed within a cavity defined within one of the shaft members. In other aspects according to the present disclosure, the nerve monitoring probe is disposed adjacent to one of the shaft members when disposed in the at rest position.

In aspects according to the present disclosure, the nerve monitoring probe includes a trigger configured to move a knife between a retracted position relative to the jaw members to an extended position between the jaw members to cut tissue disposed therebetween. In other aspects according to the present disclosure, the trigger moves in a linear fashion along the longitudinal axis to move the knife between positions. In still other aspects according to the present disclosure, the nerve monitoring probe is only deployable when the knife is disposed in a retracted position. In yet other aspects according to the present disclosure, the nerve monitoring probe is only activatable when the knife is disposed in a retracted position.

BRIEF DESCRIPTION OF THE DRAWINGS

Various aspects and features of the present electrosurgical forceps are described hereinbelow with reference to the drawings wherein like numerals designate identical or corresponding elements in each of the several views.

DETAILED DESCRIPTION

The present disclosure describes electrosurgical forceps for grasping, treating, and/or dividing tissue. The forceps includes two shafts each having a jaw member disposed at a distal end thereof and movable between open and closed positions to grasp tissue. The electrosurgical forceps also includes a knife configured to divide grasped tissue following treatment of the tissue (e.g., a tissue seal cycle). A knife lockout works in conjunction with the shafts to prevent deployment of the knife prior to the shafts reaching a sufficiently-approximated position corresponding to a sufficiently-closed position of jaw members as well as to prevent deployment of the knife during treatment of tissue. A nerve monitoring probe is included with the forceps that is selectively positionable to stimulate surround nerves with a conventional EMG monitoring system.

Figure 1:
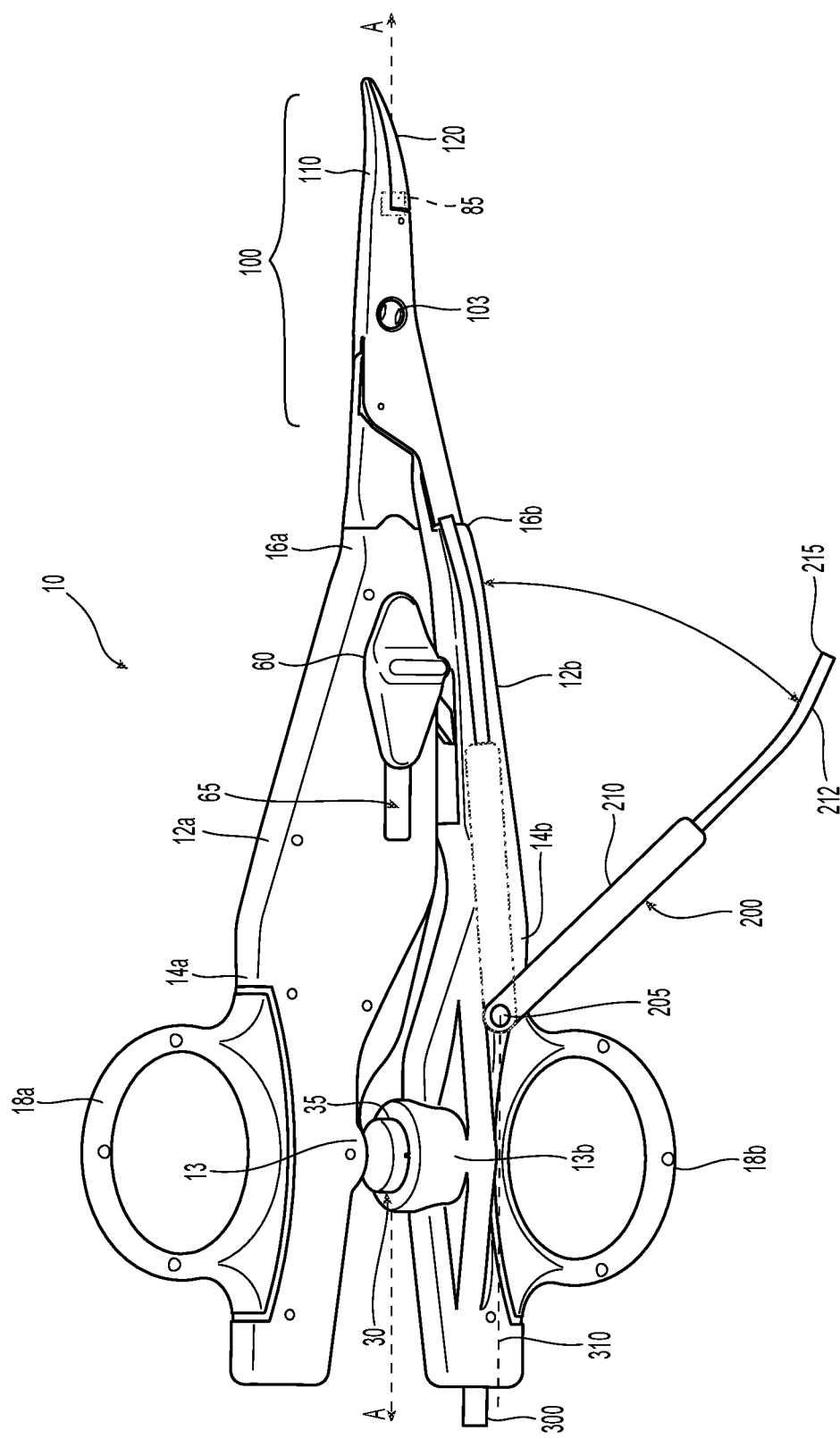
FIG. 1 is a side, perspective view of an electrosurgical forceps including a nerve monitoring probe shown in a deployed position.

Referring generally to FIG. 1, a forceps 10 provided in accordance with the present disclosure includes first and second shafts 12a, 12b each having a proximal end portion 14a, 14b and a distal end portion 16a, 16b. An end effector assembly 100 of forceps 10 includes first and second jaw members 110, 120 extending from distal end portions 16a, 16b of shafts 12a, 12b, respectively. Forceps 10 further includes a pivot member 103 pivotably coupling first and second shafts 12a, 12b with one another, a knife 85, a knife deployment trigger 60, and a switch assembly 30 including a depressible activation button 35 for enabling the selective supply of electrosurgical energy (monopolar or bipolar) to end effector assembly 100. An electrosurgical cable 300 electrically couples forceps 10 to a source of energy, e.g., an electrosurgical generator (G), to enable the supply of electrosurgical energy to jaw members 110, 120 of end effector assembly 100 upon activation of switch assembly 30. Cable 300 may include an additional electrical lead 310 that connects the generator (with an internal/external NIM system for EMG monitoring) to a nerve monitoring probe 200 as explained in more detail below. Cable 300 and lead 310 may be bundled or part of separate electrical cables depending upon a particular purpose.

The internal working components of various forceps similar to the forceps 10 of FIG. 1 are disclosed in commonly-owned U.S. patent application Ser. No. 15/617,283 and U.S. Provisional Patent Application No. 62/990,277, the entire contents of both of which being incorporated by reference herein.

Continuing with reference to FIG. 1, a knife deployment trigger 60 is coupled to shaft 12a and extends from either side of shaft 12a. The linear design of the trigger 60 is configured to inhibit the trigger 60 from catching on the surgeon, patient, or on nearby objections during use and/or as forceps 10 is inserted and withdrawn from the surgical site. More particularly, trigger 60 is actuated linearly along longitudinal axis "A-A" defined between shafts 12a, 12b to advance the knife 85 through tissue disposed between jaw members 110, 120 of end effector assembly 100. As such, the trigger 60 does not extend beyond the periphery of either shaft 12a, 12b during the range of linear motion.

Trigger 60 in an un-actuated position wherein the knife 85 is disposed in a retracted position within a knife channel (not shown) defined between the jaw members 110, 120 exposes a trigger channel 65 along shaft 12a. Trigger 60 in a proximal, actuated position deploys the knife 85 between jaw members 110, 120 to cut tissue. In this position, the trigger 60 covers the trigger channel 65 to reduce the chances of pinching a surgical glove or finger during repeated actuation. Trigger 60 may be symmetric on both sides of shaft 12a allowing actuation by right or left-handed surgeons or may be disposed on a single-side.

Details relating to the operation of trigger 60 and the internal working component thereof are disclosed in commonly-owned U.S. Provisional Patent Application No. 62/990,277, the entire contents of which being incorporated by reference herein.

Switch assembly 30 includes an activation button 35 disposed on shaft 12b in vertical opposition to an activation tab 13 disposed on shaft 12a. To initiate the supply of energy from the energy source (generator "G") to jaw members 110, 120 for sealing tissue grasped between jaw members 110, 120, shafts 12a, 12b are approximated such that tab 13 is urged into activation button 35 to activate switch assembly 30. Premature cutting of the tissue may be prevented by one or more electrical or mechanical knife lockouts such as those described with respect to either of the above-identified, commonly-owned patent applications incorporated by reference herein. In this manner, premature cutting of tissue during delivery of energy to tissue via jaw members 120, 120 (e.g., prior to completion of a tissue sealing cycle) is prevented.

Once a tissue sealing cycle is complete, switch assembly 30 may be deactivated by returning shafts 12a, 12b from an energy delivery position to a position such that jaw members 110, 120 remain in the closed position but depressible button 35 is no longer depressed by tab 13 of shaft 12a. Accordingly, trigger 60 may be actuated, as detailed above, to advance knife 85 from the retracted position towards the extended position to cut tissue grasped between jaw members 110, 120 (e.g., subsequent to completion of sealing the grasped tissue). Following cutting of the grasped tissue, shafts 12a, 12b may be moved apart from one another, as detailed above, to a spaced-apart position to reset the knife 85 to the retracted position.

Details relating to the operation of the switch assembly 30 are disclosed in commonly-owned U.S. patent application Ser. No. 15/617,283.

Turning now to the description of the nerve monitoring probe (NMP) 200 operably associated with the forceps 10, FIG. 1 shows the range of operation of the nerve monitoring probe 200 relative to the forceps 10. More particularly, NMP 200 includes a generally elongated housing 210 having a monitoring portion 212 that extends therefrom that terminates at a tip 215 configured to engage tissue. Housing 210 operably couples to shaft 12b about a pivot 205 that is configured to allow selective rotation of the NMP 200 between an at rest position disposed within or adjacent shaft 12b and a deployed position wherein the NMP 200 is rotated relative to shaft 12b and at an angle relative to longitudinal axis A-A for use. NMP 200 may be repeatedly rotated in and out of deployment as needed during use.

Figure 2:
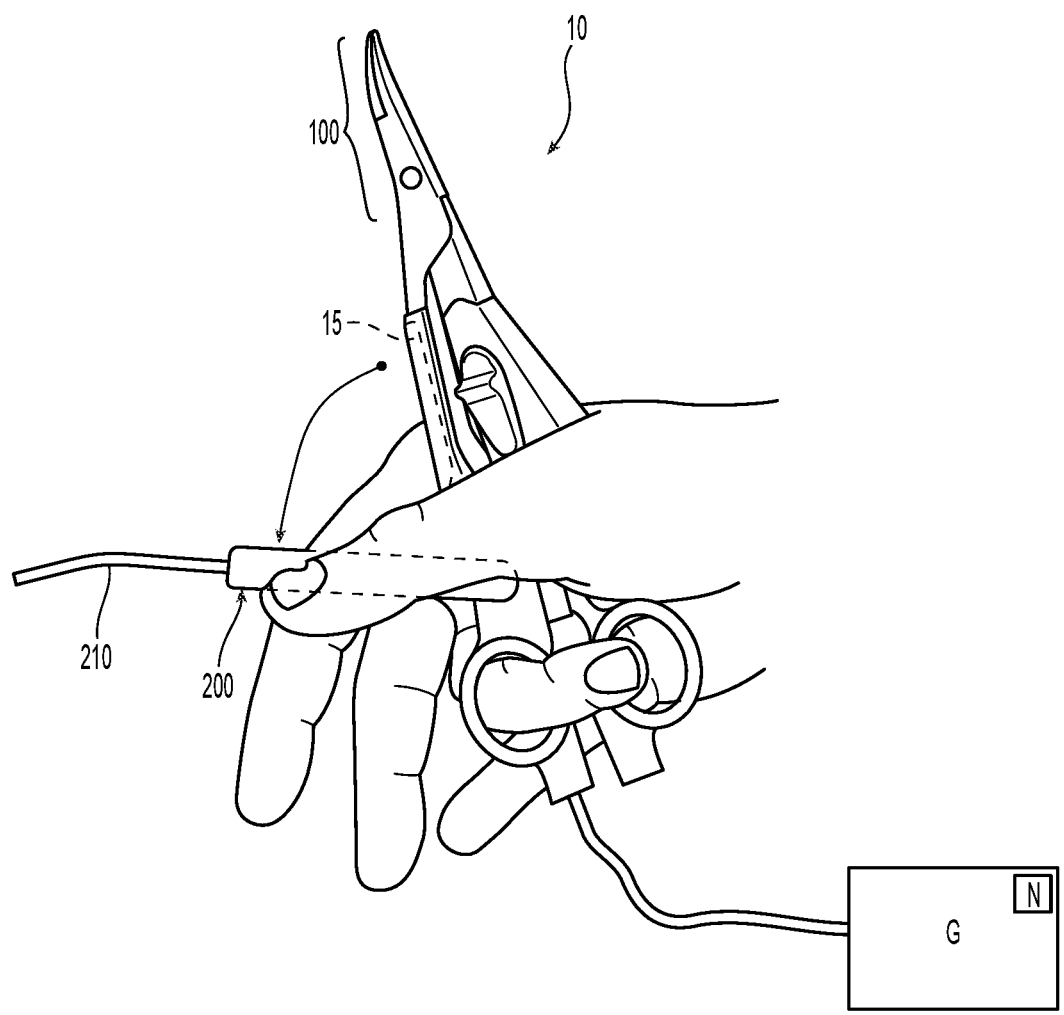
FIG. 2 is a schematic view of the electrosurgical forceps of FIG. 1 shown within the deployed position within a surgeon's hand.

Cable 310 electrically engages NMP 200 at a proximal end of the housing 210 and, ultimately, connects to a nerve monitoring system N (FIG. 2), e.g., the NIM® Nerve Monitoring System sold by Medtronic which is an electromyographic (EMG) monitor for intraoperative use during various surgeries such as ENT and general surgical procedures. Intraoperative nerve monitoring systems enable surgeons to identify, confirm, and monitor motor nerve function to help reduce the risk of nerve damage during various procedures. The nerve monitoring system N may be integrated within the electrosurgical generator G or may be a separate unit.

As mentioned above and as seen in FIG. 2, the NMP 200 may be rotated in an out of deployment from within a cavity 15 defined in shaft 12b or from a side thereof. More particularly, a surgeon's thumb may be positioned to easily deploy the NMP 200 from within cavity 15 (or a side of shaft 12b) when needed during surgery. After use, the surgeon's thumb can easily return the NMP 200 to the at rest position.

The NMP 200 may be configured such that the NMP 200 is automatically activated when deployed or when rotated to a certain position. The NMP 200 may be configured to slide out of shaft 12b to deploy and slide back to the at rest position by a surgeon's thumb or other finger. In embodiments, the NMP 200 may be configured to only be deployable or activatable when the jaw members 110, 120 are disposed in an approximated position. In embodiments, the NMP 200 may be configured to be deployable or activatable when the jaw members 110, 120 are disposed in an open or spaced apart position.

In embodiments, the NMP 200 may be configured to only be activatable when the activation button 35 of the switch assembly 30 is deactivated or inactive.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
    first and second shaft members each having a jaw member disposed at a distal end thereof, the first and second shaft members configured to rotate about a first pivot to move the jaw members between an open position and a closed position, the first and second shaft members defining a longitudinal axis therebetween; and
    a nerve monitoring probe having a housing and a monitoring portion, the housing operably coupled to a first shaft member about a second pivot proximal to the first pivot, the nerve monitoring probe selectively movable relative to the longitudinal axis between a first, at rest position wherein the nerve monitoring probe is aligned with the longitudinal axis and a second, deployed position wherein the nerve monitoring probe is positioned at an angle relative to the longitudinal axis for nerve monitoring.

2. The electrosurgical forceps according to claim 1 wherein the nerve monitoring probe is automatically activated when disposed in the deployed position.

3. The electrosurgical forceps according to claim 1 wherein the nerve monitoring probe is adapted to connect to an electrosurgical generator including a nerve monitoring system.

4. The electrosurgical forceps according to claim 1 wherein the nerve monitoring probe is adapted to connect to a nerve monitoring system.

5. The electrosurgical forceps according to claim 1 wherein the nerve monitoring probe is only activatable when the jaw members are disposed in an approximated position that activates a switch assembly.

6. The electrosurgical forceps according to claim 1 wherein the nerve monitoring probe is only activatable when the jaw members are disposed in an open position.

7. The electrosurgical forceps according to claim 1 wherein the nerve monitoring probe is only activatable when an activation button is inactive.

8. The electrosurgical forceps according to claim 1 wherein the nerve monitoring probe is housed within a cavity defined within the first shaft member.

9. The electrosurgical forceps according to claim 1 wherein the nerve monitoring probe is disposed adjacent the at least one shaft member when disposed in the at rest position.

10. The electrosurgical forceps according to claim 1, further comprising:
    a trigger configured to move a knife between a retracted position relative to the jaw members to an extended position between the jaw members to cut tissue disposed therebetween.

11. The electrosurgical forceps according to claim 10 wherein the trigger moves in a linear fashion along the longitudinal axis to move the knife between positions.

12. The electrosurgical forceps according to claim 10 wherein the nerve monitoring probe is only deployable when the knife is disposed in a retracted position.

13. The electrosurgical forceps according to claim 10 wherein the nerve monitoring probe is only activatable when the knife is disposed in a retracted position.

* * * * *